(12) United States Patent
Lepetitcorps et al.

(10) Patent No.: US 7,608,283 B2
(45) Date of Patent: Oct. 27, 2009

(54) CORAL PURIFICATION METHOD AND CORAL THUS OBTAINED

(75) Inventors: Yann Lepetitcorps, Leognan (FR); Jean-Christophe Fricain, Bordeaux (FR); Vincent Souillac, Bordeaux (FR); Alain Largeteau, Cestas (FR); Roland Schmitthaeusler, Montigny le Bretonneux (FR)

(73) Assignee: Biocoral Inc., Wilminton, DE (US)

( * ) Notice: Subject to any disclaimer, the term of this patent is extended or adjusted under 35 U.S.C. 154(b) by 372 days.

(21) Appl. No.: 10/581,273

(22) PCT Filed: Dec. 6, 2004

(86) PCT No.: PCT/FR2004/003126

§ 371 (c)(1),
(2), (4) Date: Jun. 1, 2006

(87) PCT Pub. No.: WO2005/055885

PCT Pub. Date: Jun. 23, 2005

(65) Prior Publication Data

US 2007/0100134 A1     May 3, 2007

(30) Foreign Application Priority Data

Dec. 5, 2003   (FR) .................................. 03 14299

(51) Int. Cl.
*A61K 35/12* (2006.01)
*A61K 38/00* (2006.01)
*C07F 3/24* (2006.01)

(52) U.S. Cl. .......................... 424/520; 514/21; 435/262

(58) Field of Classification Search ...................... None
See application file for complete search history.

(56) References Cited

U.S. PATENT DOCUMENTS

| | | | |
|---|---|---|---|
| 4,990,333 A | * | 2/1991 | Lane et al. .................. 424/551 |
| 5,723,012 A | | 3/1998 | Fages et al. |
| 6,217,614 B1 | | 4/2001 | Fages et al. |
| 6,414,050 B1 | | 7/2002 | Howdle et al. |
| 6,579,532 B1 | | 6/2003 | Mandel et al. |

FOREIGN PATENT DOCUMENTS

| | | |
|---|---|---|
| CN | 1144102 | 3/1997 |
| CN | 1203189 | 12/1998 |
| CN | 1416910 | 5/2003 |
| WO | 99/02200 | 1/1999 |

OTHER PUBLICATIONS

Derwent Abstract, (CN 1144102A abstract only), 1997.*

* cited by examiner

*Primary Examiner*—David M. Naff
*Assistant Examiner*—Debbie K Ware
(74) *Attorney, Agent, or Firm*—Dennison, Schultz & MacDonald

(57) ABSTRACT

The present invention provides a method of extracting organic substances present in coral, which consists in treating the coral with a fluid or a mixture of fluids in the supercritical state without modifying the crystalline structure of said coral, at a temperature of less than 270° C. and at a pressure which is much higher than the critical pressure of said fluid or mixture of fluids, for example of the order of at least 3 times, and preferably at least 5 times said critical pressure. It also provides coral obtained by said method and bone substitutes fabricated from said coral.

10 Claims, 2 Drawing Sheets

CORAL PURIFICATION METHOD AND CORAL THUS OBTAINED

This application is a filing under 35 USC 371 of PCT/FR2004/003162, filed Dec. 6, 2004.

BACKGROUND OF THE INVENTION

The present invention relates to a method of purifying coral, and to the coral obtained by said method.

The invention is of particular application in the medical field.

Coral, which has a porous structure, is essentially (about 97%) composed of mineral material, mainly calcium carbonate, with the remainder (about 3%) being constituted by oxides of magnesium and iron together with organic substances which are responsible for its color. Its hardness varies from 2.5 to 3.5 on the Mohs scale.

The constituent calcium carbonate of coral has a metastable aragonite type crystallographic structure which can easily be transformed into calcite, especially under the effect of a temperature of about 260° C.

The organic matter in coral contains a proteinaceous material, but it is substantially free of lipid material.

Several bone substitutes based on coral currently exist and have been approved by the Agence Française de Sécurité Sanitaire des Produits de Santé (AFSSAPS) [French Health Safety Products Agency]. One of those products, sold by INOTEB under the trade name BIOCORAL®, is obtained by treating the coral at the surface of its pores, which can eliminate a portion of the organic substances mentioned above.

A more thorough morphological analysis of coral (thermal scanning electron microscope coupled with mass spectroscopy) shows, however, that said organic substances are present not only in the pores of the coral, but also at the grain boundaries of the calcium carbonate particles. The treatment carried out for the BIOCORAL® product cannot extract organic substances located at the grain boundaries, which represents about 90% of the total organic substances.

SUMMARY OF THE INVENTION

One problem which the present invention aims to overcome is thus to provide coral that is substantially free of organic matter, in particular proteins, and that can be used to fabricate bone substitutes with a quality comparable to that of existing synthetic implants.

The term "coral substantially free of organic matter" as used in the present description means coral containing not more than half as much organic substance as untreated coral.

A further problem which the present invention aims to overcome is to provide a method which can eliminate organic substances present in the coral without modifying its crystalline structure.

It has now been discovered, and this forms the basis of the invention, that treating coral with a fluid under supercritical conditions in an optimized temperature and pressure range can overcome the problems mentioned above, which problems are not overcome with known prior art methods.

Hence, in a first aspect, the invention provides a method of extracting organic substances present in coral, which method consists in treating the coral with a fluid or a mixture of fluids in the supercritical state without modifying the crystalline structure of said coral, at a temperature of less than 270° C., preferably 260° C. or less, and more preferably 250° C. or less, and at a pressure which is much higher than the critical pressure of said fluid or mixture of fluids, for example of the order of at least 3 times, and preferably at least 5 times said critical pressure.

The use of a fluid in a supercritical state to extract organic substances has been described in European patent document EP-A-0 603 920. However, that document relates only to the treatment of a bone tissue and uses carbon dioxide to extract lipids, i.e. substances which are not found in coral. According to that document, in order to extract proteins, a complementary chemical or enzymatic treatment is employed that makes use of additional compounds such as detergents or oxidizing agents, which would alter the structure of the coral. Further, in that document, the treatment is carried out at a pressure close to the critical pressure of carbon dioxide.

In the method of the invention, a fluid is used under conditions that are termed "supercritical", i.e. the fluid has the invasive properties of a gas while behaving like a liquid. For this reason, the fluid can diffuse into the porous structure of the coral without any wettability problems, which can optimize extraction of the organic substances present in the coral, in particular proteins (which are also termed below the "organic matrix").

The fluid or the mixture of fluids suitable for use in the method of the invention must have a critical temperature of less than 270° C., preferably 260° C. or less, and more preferably 250° C. or less, and must dissolve organic matter.

Examples which may be mentioned are ethanol, acetone, or a mixture of one of those two fluids with carbon dioxide and having a critical temperature of less than 270° C. Advantageously, ethanol is used because of its availability and its inexpensive and non toxic nature. The critical temperature of ethanol is 240° C. and its critical pressure is 6.12 MPa [megapascals].

When the fluid is ethanol or acetone, the treatment temperature for the coral is advantageously in the range 240° C. to 260° C.

When a mixture of fluids is used such as an ethanol-carbon dioxide mixture, the coral treatment temperature is advantageously in the range 80° C. to 100° C.

The method of the invention is carried out at a sufficient pressure which is much higher than the critical pressure of the fluid or mixture of fluids used to prevent transformation of the crystalline structure of the coral. In this regard, the critical pressure of the fluids mentioned above is easily achieved.

With ethanol or acetone, the coral treatment pressure is advantageously in the range 300 MPa to 450 MPa, preferably in the range 350 MPa to 450 MPa.

With a mixture of fluids such as an ethanol and carbon dioxide mixture, the coral treatment pressure is advantageously in the range 30 MPa to 50 MPa, preferably of the order of 40 MPa.

The treatment period is not critical per se and generally varies between a few minutes and a few hours depending on the fluid used. In the case of ethanol or acetone, this period is advantageously in the range 15 min [minutes] to 240 min, and preferably about 1 h [hour].

Given the mineral chemical composition of coral, the fluid or mixture of fluids of the invention is advantageously used without any additional compound such as a detergent or oxidizing agent which could alter the structure of the coral.

In a second aspect, the invention concerns coral substantially free of organic substances, as obtained by the method described above.

In a third aspect, the invention provides bone substitutes produced from coral substantially free of organic substances.

Said bone substitutes may be obtained using methods that are well known to the skilled person.

BRIEF DESCRIPTON OF THE DRAWINGS

The invention is illustrated below using the following examples, and the accompanying drawing figures, in which.

EXAMPLE 1

Supercritical Treatment of Coral

Untreated coral was treated in a high water pressure generating device in a chamber with a fixed volume. This chamber, produced from a high strength alloy, was 229 mm [millimeters] deep and had an inside diameter of 55 mm. It was closed by a mushroom-shaped closure supporting the metallic seal which provided a seal by deformation thereof. The seal on start-up (without the autoclave being pressurized) was produced by raising the closure using 8 screws in the upper portion. The pressure applied to the chamber by the pump or the temperature compress the seal and thus seal the system.

The temperature was measured inside the chamber using a thermocouple mounted in the upper portion of the reactor. It was in direct contact with the pressurized fluid.

The coral was placed in flexible 20 mL [milliliter] Teflon PFA bottles (ref M77400, Fisher Bioblock Scientific) which can resist temperatures of close to 300° C. and tolerate deformation due to pressure. Equal pressures were exerted on the inside and outside walls of the bottle. Since the bottle contained very little or no air, the liquid present inside the bottle and the transmitting liquid (water) were at the same pressure, and thus the wall was only deformed slightly due to the compressibility of water. The treatment was carried out in the presence of ethanol as the "supercritical" fluid at a temperature of 240° C. to 260° C., preferably of the order of 250° C., and at a pressure of 300 MPa to 400 MPa, preferably of the order of 350 MPa for 15 min to 240 min, preferably for about 1 h.

EXAMPLE 2

Determination of the Quantity of Residual Organic Substances in the Treated Coral The sample obtained in Example 1 was ground with a mortar and weighed (UM mass—untreated matter—about 3 g [grams]). 3 g of the powder obtained was dissolved in 135 mL of 0.1N HCl with stirring for 1 h. The solution obtained thereby was dialyzed through a membrane with a molecular weight of 12000 to 16000 (reference MCWO) then frozen at −80° C. and freeze dried. The freeze dried material was then weighed (OM mass—organic matter—about 3 g.

For comparison purposes, the same experiment was carried out on an untreated coral sample (aragonite) and on a sample of BIOCORAL®.

Figure 1:
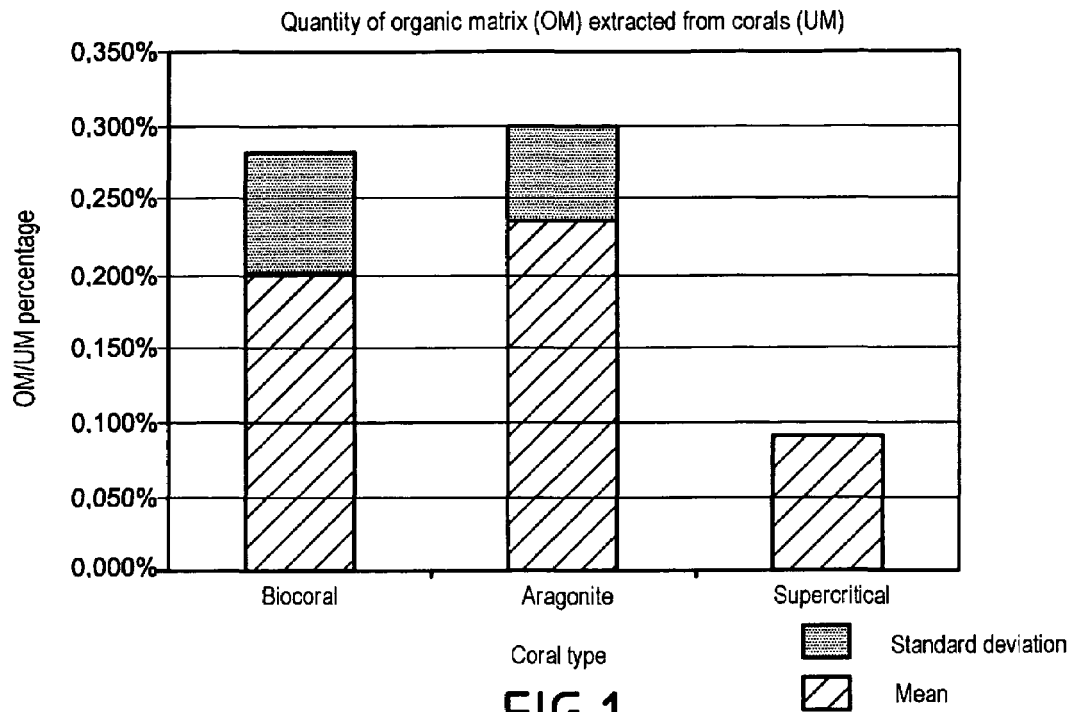
FIG. 1 is a graph showing the ratio of organic matter to total mass for a coral sample treated according to the invention, and two comparative samples.

FIG. 1 shows the ratio OM/UM for each of the three samples. It can be seen that the "supercritical" treatment of the invention can produce a coral containing about half the organic substances as the BIOCORAL® product.

EXAMPLE 3

Determination of the Quantity of Residual Proteins in Treated Coral

1/ Preparation of Working Solution and Samples:
50 volumes of solution A was mixed with 1 volume of solution B. The working solution was slightly cloudy to start with, then cleared rapidly with gentle vortex stirring. It was an opalescent green color;
the samples were ground with a mortar and the powder obtained was weighed;
1 g of powder was dissolved in 45 mL of 0.6N HCl over 1 hour, with stirring.

2/ Procedure for Determination:
the water-soluble fraction was assayed in water: 1.2 mg [milligrams] of organic matter was dissolved in 75 μL [microliters] water;
the residue following centrifuging was dissolved in 75 μL of 0.3N NaOH;
25 μL of each standard (0 μg/mL, 5 μg/mL, 25 μg/mL, 50 μg/mL and 250 μg/mL [micrograms/milliliter]) of each sample (prepared in the same manner as the assay samples) and they were distributed into wells of a 96-well plate;
the plate was covered and incubated for 30 min at 37° C.;
the optical density at 562 nm [nanometers] was read once the plate had cooled to ambient temperature.

For comparison, the same experiment was carried out on a sample of raw coral (aragonite) and on a sample of BIOCORAL®.

Figure 2:
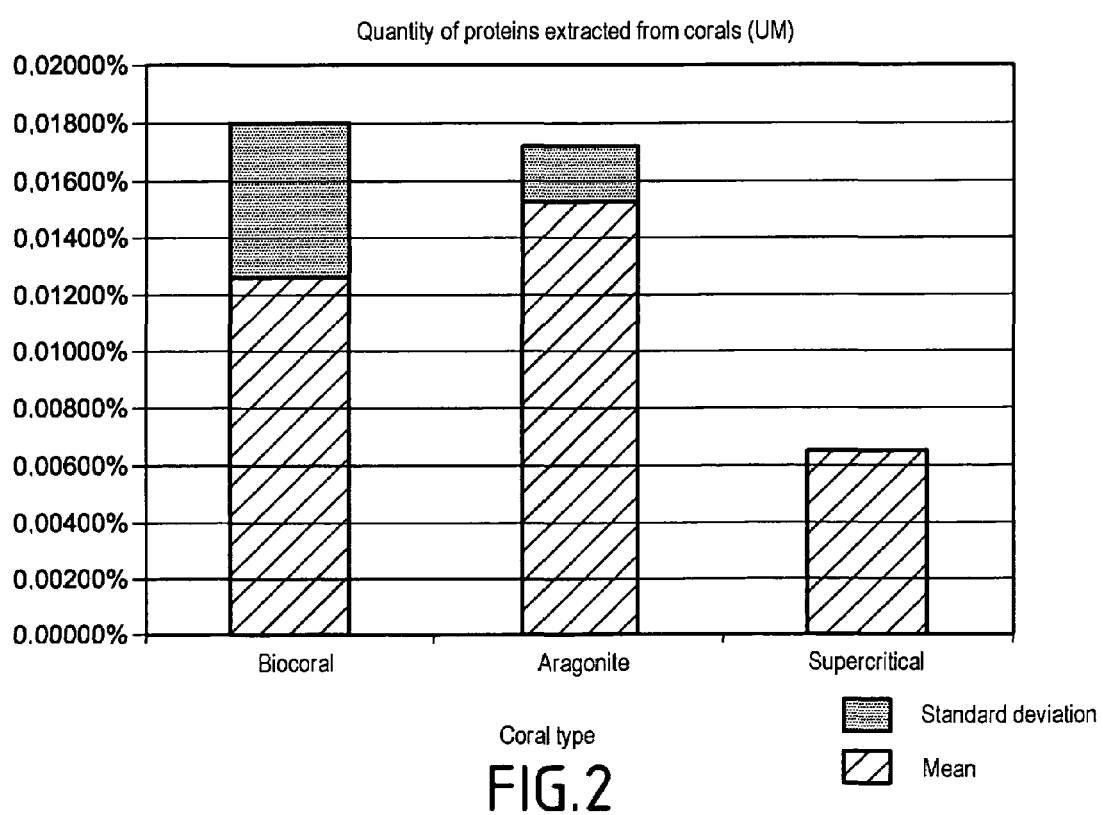
FIG. 2 is a graph showing the ratio of residual protein to total mass for a coral sample treated according to the invention, and two comparative samples.

FIG. 2 shows the protein/UM ratio for each of the three samples. It can be seen that the "supercritical" treatment of the invention can produce a coral from which about twice as much protein has been extracted compared with the BIOCORAL® product.

EXAMPLE 4

Demonstrating Cell Proliferation of Bone Cells on Treated Coral

Cylinders (diameter=12 mm) were cut into 1 mm thick disks using a diamond saw then sterilized by dry heat at 100° C. for 1 h 30 (3 cycles). The disks were deposited on a bed of 0.1% agarose in culture dishes (NUNC; 24 wells, 2 cm$^2$ [square centimeters]). The cell suspension was deposited onto each disk in an amount of 20000 MG63 cells/cm$^2$ (1.13 cm$^2$×2, since porosity—22600 cells, i.e. about 50000 cells per sample), in a volume of 100 μL of complete culture medium (IMDM: Iscowe's Modified Dubelcco's Medium, 10% FCS—fetal calf serum). After 30 min to allow the cells to adhere, it was supplemented with 1 mL of medium. The medium was changed every two days.

The complete culture medium was removed and rinsed with medium alone. The cells were starved for 17 hours (medium alone+10% FCS, tritiated thymidine, 10 μCi/mL [microcuries/milliliter] (ref: TRK 758 AMERSHAM), i.e. 10 μL of $^3$HT/volume of complete medium). The supernatant was eliminated (retained for subsequent elimination) then the material was removed from the agarose and it was transferred to a plastic well. It was rinsed twice with PBS 1× (or Hank's 1×), then the cells were fixed with cold 100% methanol, for 10 min at 4° C. It was rinsed twice with PBS 1× (or Hank's 1×)

and precipitated with cold 5% TCA for 20 minutes at 4° C. The supernatant was eliminated and it was rinsed four times with PBS 1× (or Hank's 1×).

It was incubated in 0.3N NaOH for 2 h at ambient temperature (to dissolve the cell layer) without exceeding 300 µL to 500 µL of NaOH. The solution was recovered in a scintillation tube to which 5 mL of liquid scintillant had been added, and the radioactivity of the solution and the material were determined using a β counter (negligible radioactivity).

For comparison, the same experiment was carried out on a sample of untreated coral (aragonite) and on a sample of BIOCORAL®.

Figure 3:
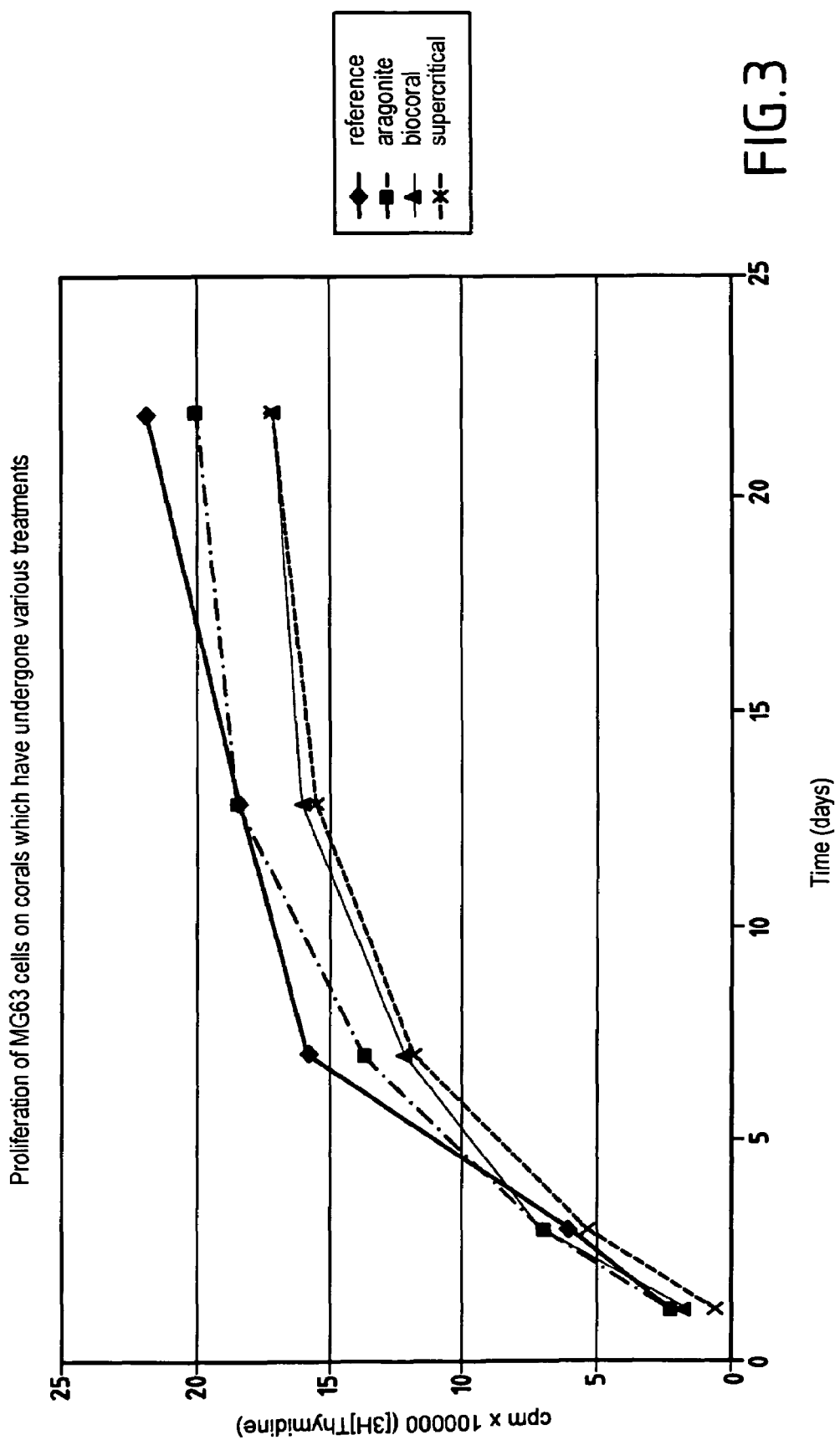
FIG. 3 is a graph of proliferation of bone cells vs. time on a coral sample treated according to the invention, and comparative samples.

The results are shown in FIG. 3. It can be seen that cell proliferation of MG63 cells on the coral treated in accordance with the invention was identical to that observed with the BIOCORAL® product.

These results suggest that coral treated in accordance with the present invention may be used in the fabrication of bone substitutes.

The invention claimed is:

1. A method of extracting organic substances present in coral, comprising treating the coral with a fluid or said fluid in a mixture of fluids in a supercritical state without modifying the crystalline structure of said coral, at a temperature of less than 270° C., and at a pressure which is higher than the critical pressure of said fluid or mixture of fluids.

2. A method according to claim 1, in which said fluid is selected from the group consisting of ethanol and acetone.

3. A method according to claim 1, in which said fluid is ethanol.

4. A method according to claim 3, in which the coral treatment pressure is in the range 300 MPa to 450 Mpa.

5. A method according to claim 4, in which the coral treatment temperature is in the range 240° C. to 260° C., and the coral is treated for a period in the range 15 min to 240 min.

6. A method according to claim 1, in which the mixture of fluids is an ethanol and carbon dioxide mixture, and the coral treatment pressure is in the range 30 MPa to 50 MPa.

7. A method according to claim 6, in which the coral treatment temperature is of the range of 80° C. to 100° C.

8. A method according to claim 1, in which said mixture of fluids is selected from the group consisting of ethanol and carbon dioxide mixtures, and acetone and carbon dioxide mixtures, the critical temperature of said mixture being less than 270° C.

9. A method according to claim 3, in which the coral treatment pressure is in the range 350 MPa to 400 MPa.

10. A method of extracting organic substances present in coral, comprising treating the coral with a fluid or said fluid in a mixture of fluids in a supercritical state without modifying the crystalline structure of said coral, at a temperature of less than 270° C. and at a pressure which is at least 3 times higher than the critical pressure of said fluid or mixture of fluids.

* * * * *